(12) United States Patent
Nabavian

(10) Patent No.: US 12,251,329 B1
(45) Date of Patent: Mar. 18, 2025

(54) NASAL SPLINT DEVICE

(71) Applicant: Ryzera Corp., Columbia, MD (US)

(72) Inventor: Reza Nabavian, Columbia, MD (US)

(73) Assignee: Ryzera Corp., Columbia, MD (US)

( * ) Notice: Subject to any disclaimer, the term of this patent is extended or adjusted under 35 U.S.C. 154(b) by 153 days.

(21) Appl. No.: 16/595,246

(22) Filed: Oct. 7, 2019

(51) Int. Cl.
*A61F 5/08* (2006.01)
*A61F 5/01* (2006.01)

(52) U.S. Cl.
CPC ........ *A61F 5/08* (2013.01); *A61F 2005/0197* (2013.01)

(58) Field of Classification Search
CPC .. A61F 5/08; A61F 5/01; A61F 5/0102; A61F 5/0104; A61F 5/058; A61F 5/05825; A61F 5/05883; A61F 5/05891; A61F 2005/0197; A61F 2013/00361; A61F 2013/0037; A61F 2013/00374; A61F 2013/00476; A61F 13/04; A61F 13/048; A61F 13/12; A61F 13/126; A61F 5/00; A61F 5/04; A61F 2013/00365
USPC .......................... 602/5, 6; 128/845, 857, 858
See application file for complete search history.

(56) References Cited

U.S. PATENT DOCUMENTS

| | | | | |
|---|---|---|---|---|
| 4,213,452 | A * | 7/1980 | Shippert | A61F 5/08 D24/189 |
| 5,718,224 | A * | 2/1998 | Muchin | A61F 5/08 606/204.45 |
| 5,961,537 | A * | 10/1999 | Gould | A61F 5/08 606/204.45 |
| 6,065,470 | A * | 5/2000 | Van Cromvoirt | A61F 5/08 128/200.24 |
| 2008/0082030 | A1* | 4/2008 | Clark | A61F 5/08 606/204.45 |
| 2013/0118488 | A1* | 5/2013 | Ledogar | A61F 5/08 128/203.12 |
| 2013/0190807 | A1* | 7/2013 | Andis | A61F 5/08 606/204.45 |
| 2016/0220251 | A1* | 8/2016 | Gozar | A61B 17/122 |
| 2018/0153728 | A1* | 6/2018 | Le | A61F 5/08 |

* cited by examiner

Primary Examiner — Caitlin A Carreiro
(74) Attorney, Agent, or Firm — Patent Law Works LLP

(57) ABSTRACT

A nasal splint device and method of using the nasal splint device, configured to maintain the desired effect of surgery, facilitate healing, and ease discomfort during post-operative care after surgery. In particular, the present invention relates to embodiments of a versatile, removable, hypoallergenic nasal splint for post-operative care after rhinoplasty or nose surgery. The nasal splint device comprises an outer layer serving as a semi-rigid frame over an inner layer that is flexible, soft, and/or malleable and configured to sit against or contour along a patient's nose.

20 Claims, 5 Drawing Sheets

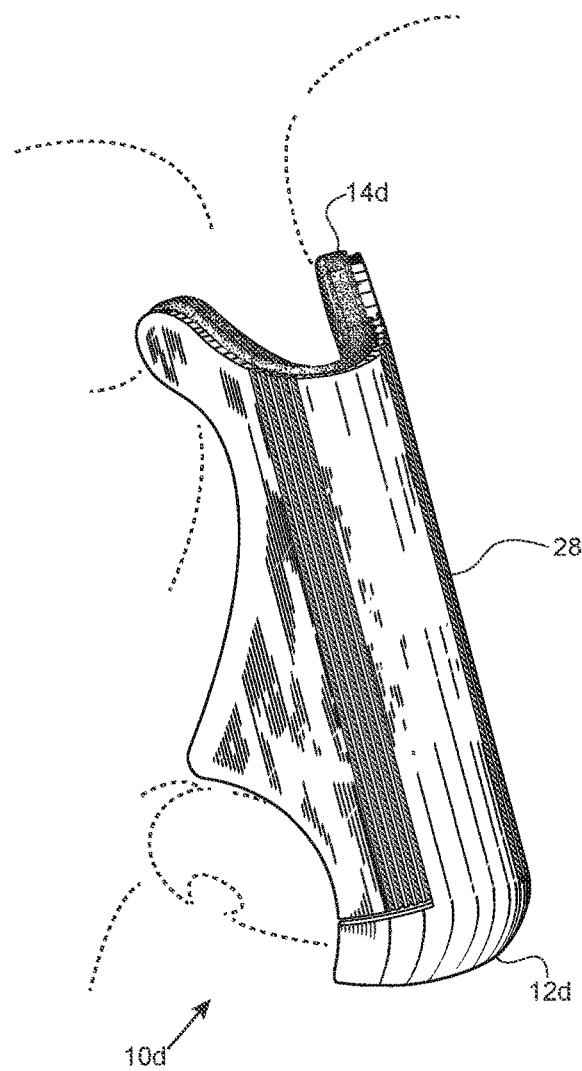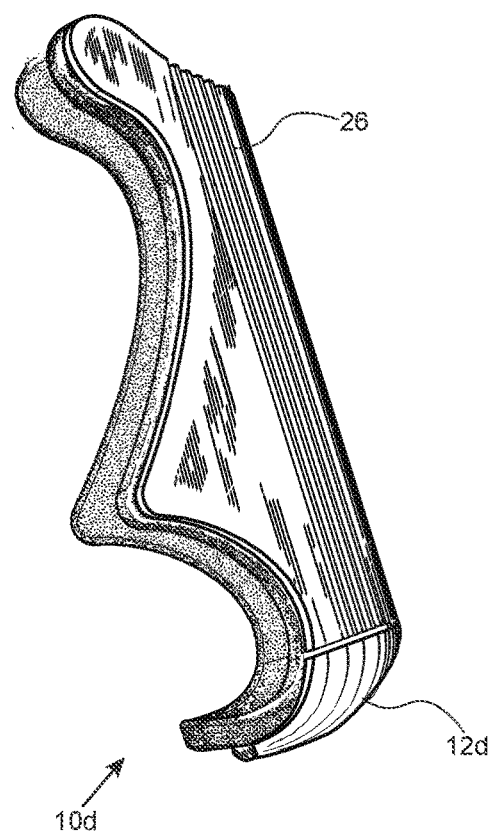
Figure 7
Figure 8

NASAL SPLINT DEVICE

FIELD OF THE INVENTION

The present invention relates to an apparatus or device and method for constructing and using the device to enhance the intended effect of surgery, facilitate healing, and generally ease discomfort experienced by a patient during the critical post-operative period following surgery. In particular, the present invention relates to embodiments of a versatile, removable, hypoallergenic nasal splint device configured for use during post-operative care after rhinoplasty or nose surgery.

BACKGROUND OF THE INVENTION

Cosmetic surgery is a unique discipline of medicine focused on enhancing appearance through surgical and medical techniques. Cosmetic surgery can be performed on all areas of the head, face, neck and body. Because treated areas function properly but lack aesthetic appeal, cosmetic surgery is elective. In particular, rhinoplasty, referred to as a "nose job" or "nose reshaping" by patients, enhances facial harmony and the proportions of a person's nose. It can also correct impaired breathing caused by structural defects in the nose.

Rhinoplasty is associated with many risks, not just medical, but unfulfilled expectations of the patient. Postoperative deformities and other risks and complications have to be considered. Complications of skin and soft tissues surrounding the surgical areas can be atrophy, fibrosis, numbness, cysts originating from displaced mucosa or subcutaneous granulomas caused by ointment material. Postoperative swelling depends mainly on the osteotomy technique. Percutaneous osteotomies cause less trauma, but may result in visible scars.

Typically, there is prolonged tissue swelling after rhinoplasty. An external splint, applied after surgery, increases a patient's compliance with post-operative care and provides quicker and better results. Prolonged swelling can lead to fibrosis that can adversely affect the surgical outcome and require painful injections and possibly re-operation in some cases.

Current splints cannot be removed by patients themselves, without potential harm to the injured areas. Therefore, the doctor is required to remove the initial splint after five to ten days. Some patients use tapes on the nose to protect the affected area, but tapes don't apply uniform and effective pressure and can instead lead to rashes and skin irritation. Also, the act of placing tapes and removing them over injured skin is traumatic.

Therefore, there is a need in the field to develop healing devices, in particular, a nasal device configured to address and improve the post-operative care following rhinoplasty. A need exists for a nose splint that can avoid painful adhesive attachment, address patient comfort, and preserve the desired outcome of surgery.

SUMMARY OF THE INVENTION

The present invention teaches, depicts, enables, illustrates, describes and claims embodiments of a new, useful, and non-obvious apparatus and method of providing post-operative care. In particular, the present invention provides embodiments of a nasal splint or device, configured to maintain the desired effect of surgery, facilitate healing, and ease discomfort. The nasal splint or device is configured to engage an exterior tissue region of a patient's or person's nose. The nasal splint or device is for use during post-operative care immediately following surgery of a nose or a rhinoplasty procedure. The nasal splint is configured to be versatile, removable, and hypoallergenic for post-operative care after rhinoplasty or nose surgery.

As illustrated by the various embodiments, the nasal splint device comprises an outer layer serving as a semi-rigid frame over an inner layer that is flexible, soft, and/or malleable and configured to sit against or contour along a patient's nose.

In accordance with a first embodiment, the nasal splint device is configured to position over a patient's nose such that the outer layer serves as a semi-rigid frame over an inner layer that is flexible, soft, and/or malleable and configured to sit against or contour the exterior of the patient's nose. The outer layer is compressible by a tubular spring mechanism configured within the nasal splint, which is located in the top portion of the outer layer and configured to vary the pressure applied on the nose. The outer layer compressible by the tubular spring mechanism includes two identical compression springs, positioned between two opposing flanges of the outer layer and configured to gently vary the pressure applied on the nose as desired by the surgeon or post-operative care doctors. The outer layer gently applies the desired pressure to maintain the shape of the nose, while the inner layer cushions and protects the delicate area where the surgery occurred.

In accordance with a second embodiment, the nasal splint device is configured to position over a patient's nose such that an outer layer serves as a semi-rigid or resilient frame over an inner layer that is flexible, soft, and/or malleable and configured to sit against or contour the exterior of the patient's nose. The outer layer is compressible by a flat spring mechanism located and positioned over the outer layer and configured to vary the pressure applied on the nose. In some embodiments, the flat spring mechanism is configured to be removed or gently slide into place over the outer layer.

In accordance with a third embodiment, the nasal splint is configured to position over a patient's nose such that its outer layer serves as a semi-rigid frame over an inner layer that is flexible, soft, and/or malleable and configured to sit against or contour the exterior of a patient's nose. The outer layer has two projecting flanges (on either side) held by two parallel springs between them, configured to move the projecting flanges toward each other and away from each other to vary the pressure applied on the nose. The two springs are coiled springs held substantially in place by an eye with a nut at either end, to maintain force between two opposing sides. Applying a slight force on the protecting flanges to compress the distance between the projecting flanges can help position the nasal splint over a patient's nose.

In accordance with yet a fourth embodiment, the nasal splint is positioned over a patient's nose such that an outer layer serves as a semi-rigid frame over an inner layer that is flexible, soft, and/or malleable and configured to sit against or contour along the person's nose, the outer layer having a crimped surface and assembly (at either end) configured to vary the pressure applied on a patient's nose.

In accordance with a fifth embodiment, the nasal splint device is adapted to be positioned over a wearer's or patient's nose such that it's outer layer serves as a semi-rigid frame over an inner layer that is flexible, soft, and/or malleable and configured to sit against or contour along the exterior of a patient's nose, the outer layer with two projecting flanges (on either side) held by a knurled-nut mechanism between them, configured to move the projecting flanges to vary the pressure applied on the nose. The knurled-nut mechanism comprises a nut and a grooved pin over which the nut rolls. Moving the nut either tightens or releases the pressure on the projecting flanges by compressing or widening the distance between the projecting flanges.

BRIEF DESCRIPTION OF THE DRAWINGS

In the drawings which accompany this disclosure, like elements are referred to with common reference numerals. It should be recognized that the drawings are not rendered to scale and are merely representative of the invention.

FIG. 7 is a front, top, and side perspective view of a fourth embodiment of the nasal splint device illustrated positioned over a person's nose (shown by broken lines), with the nasal splint device comprising an outer layer serving as a semi-rigid frame over an inner layer that is flexible, soft, and/or malleable and configured to sit against or contour along the exterior of a patient's nose, the outer layer having a crimped surface mechanism and assembly configured to vary the pressure applied on the nose.

FIG. 8 is a side perspective view of the fourth embodiment of the nasal splint device.

DETAILED DESCRIPTION OF THE INVENTION

Figures 1, 2:
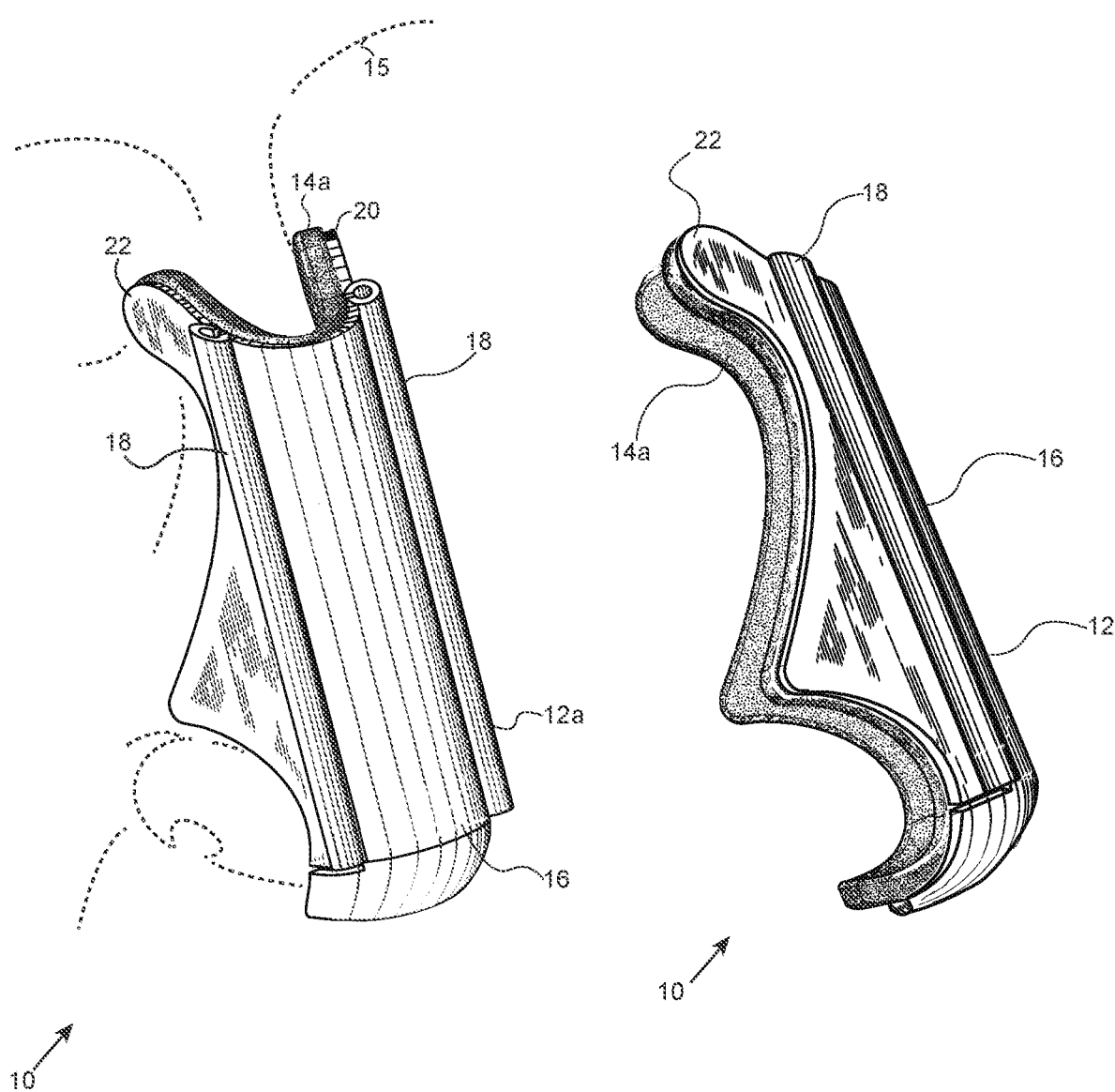
FIG. 1 is a front, top, and side perspective view of a first embodiment of the nasal splint device illustrated positioned over a patient's nose (shown by broken lines), with the nasal splint device comprising an outer layer serving as a semi-rigid frame over an inner layer that is flexible, soft, and/or malleable and configured to sit against or contour the exterior of the person's nose, the outer layer compressible by a tubular spring mechanism positioned over the top portion of the outer layer and configured to vary the pressure applied on the nose.
FIG. 2 is a side perspective view of the first embodiment of the nasal splint device.

The present invention is not limited to the illustrated or described embodiments as these are intended only to assist the reader in understanding the subject matter of the invention. The illustrated embodiments are examples of forms of the invention that are either depicted, taught, enabled, described, illustrated and claimed here. The illustrations and description cover all structures and methods which embody similar functionality. One of ordinary skill in the art will appreciate that features, devices, elements, members or components thereof, methods, processes or techniques may be applied, interchanged, eliminated in whole or part, or combined from one embodiment to another.

As illustrated in the various embodiments, the nasal splint device 10 is identified generally by reference numeral 10 in all the figures. In each of the figures illustrated, the nasal splint 10 comprises an outer layer 12 serving as a semi-rigid frame over an inner layer 14 that is flexible, soft, and/or malleable and configured to sit against or contour along a patient's nose. The nasal splint 10 adheres to and flexed across the bridge of the nose 15, illustrated in the drawings in broken lines as a portion of a human face. The inner layer 14a serves as a base layer designed to act as a buffer in engaging the patient's skin.

It should be recognized that the various members or components of the nasal splint 10, materials, layers or regions may be of differing size, area, thickness, length or shape than that illustrated or described while still remaining within the purview and scope of the present invention. The nasal splint 10 may be constructed with portions of one or more nasal splint layers to engage nasal outer wall tissues. When engaged on the nose of a wearer, preferably no portion of a layer of the nasal splint 10 extends substantially over a skin surface area beyond the surface areas associated with the nasal passages as described here. When the nasal splint 10 is flexed across the nose, separations or vertical protrusions within the nasal splint 10 change the angle, in part, of spring biasing forces, as described here, transforming the forces and imparting them, at least in part, to tissue engaging surface areas.

Referring now to FIGS. 1 and 2, in accordance with a first embodiment, the nasal splint device 10a is positioned over a patient's nose 15 (shown in broken lines) such that the outer layer 12a serves as a semi-rigid or resilient frame over an inner layer 14a that is flexible, soft, and/or malleable and configured to sit against or contour along the person's nose, the outer layer 12a compressible by a tubular spring mechanism 16 positioned over the top portion of the outer layer 12a and configured to vary the pressure applied on the nose 15. The outer layer 12a compressible by the tubular spring mechanism 16 including two identical compression springs 18, positioned between two opposing flanges 20 and 22 of the outer layer 12 are configured to vary the pressure applied on the nose. The two substantially identical compressing springs 18 are parallel to each other and designed to flank either side of the top of the patient's nose 15. The two substantially identical compression springs 18 are designed to run along the length of a patient's nose 15, biased to vary the pressure on the two opposing flanges 20 and 22. The two opposing flanges 20 and 22 gently keep the nose 15 intact and in position to facilitate healing as the patent recovers.

One type of material that may be used for the inner or base layer 14a and cover or outer layer 12a is from a group of widely available flexible nonwoven synthetic fabrics that allow the skin on user nose 11 to exchange gases with the atmosphere and to maximize comfort of the nasal splint 10 thereon. Alternatively, any suitable fabric or plastic film may be used.

In some embodiments, a continuous pressure sensitive adhesive substance, biocompatible with external human tissue, may be disposed on at least one flat surface side of said material which is the adhesive side, opposite the non-adhesive side. The non-adhesive side is typically opposite the skin engaging side. A protective layer of continuous release paper liner may cover the adhesive. The materials are typically available in continuous rolls wound in a machine direction (MD) or warp, which is perpendicular to the cross direction (XD) or fill, of the fabric. The inner or base layer 14a and outer or cover layer 12a of nasal splint 10 may be fabricated parallel to either the warp or the fill of the fabrics. In one embodiment, the outer or resilient layer 12a is a biaxially oriented polyester resin (PET). PET has suitable spring biasing properties both MD and XD, and is widely available under trade names such as Mylar® and Melinex® in a variety of standard thickness including 0.005", 0.007", and 0.010".

Figure 3:
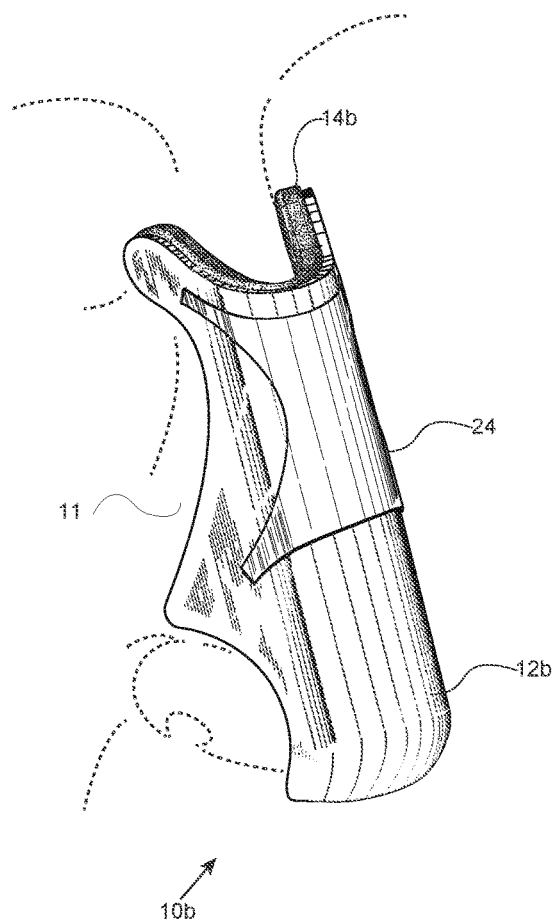
FIG. 3 is a front, top, and side perspective view of a second embodiment of the nasal splint device illustrated positioned over a person's nose (shown by broken lines), with the nasal splint device comprising an outer layer serving as a semi-rigid frame over an inner layer that is flexible, soft, and/or malleable and configured to sit against or contour the exterior of the person's nose, the outer layer compressible by a flat spring positioned over the outer layer and configured to vary the pressure applied on the nose.
Figure 4:
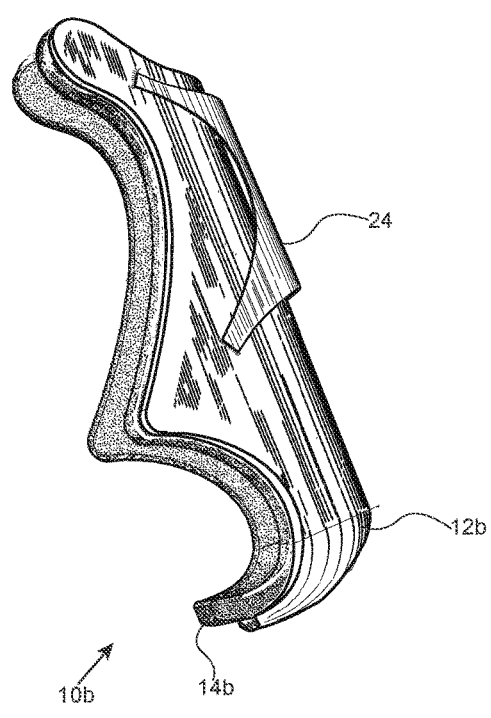
FIG. 4 is a side perspective view of the second embodiment of the nasal splint device.

In accordance with a second embodiment illustrated in FIGS. 3 and 4, the nasal splint device 10b may be positioned over a person's nose such that an outer layer 12b serves as a semi-rigid frame over an inner layer 14b that is flexible, soft, and/or malleable and configured to sit against or contour along the person's nose, the outer layer compressible by a flat spring mechanism 24 positioned over the outer layer 12b and configured to vary the pressure applied on the nose 15. The second embodiment may be constructed from similar materials as those described for embodiment one. The flat spring mechanism 24 is shaped with a scalloped edge on either side, designed and biased to gently vary the pressure on the outer layer 12b as it covers the nose 15.

Figures 5, 6:
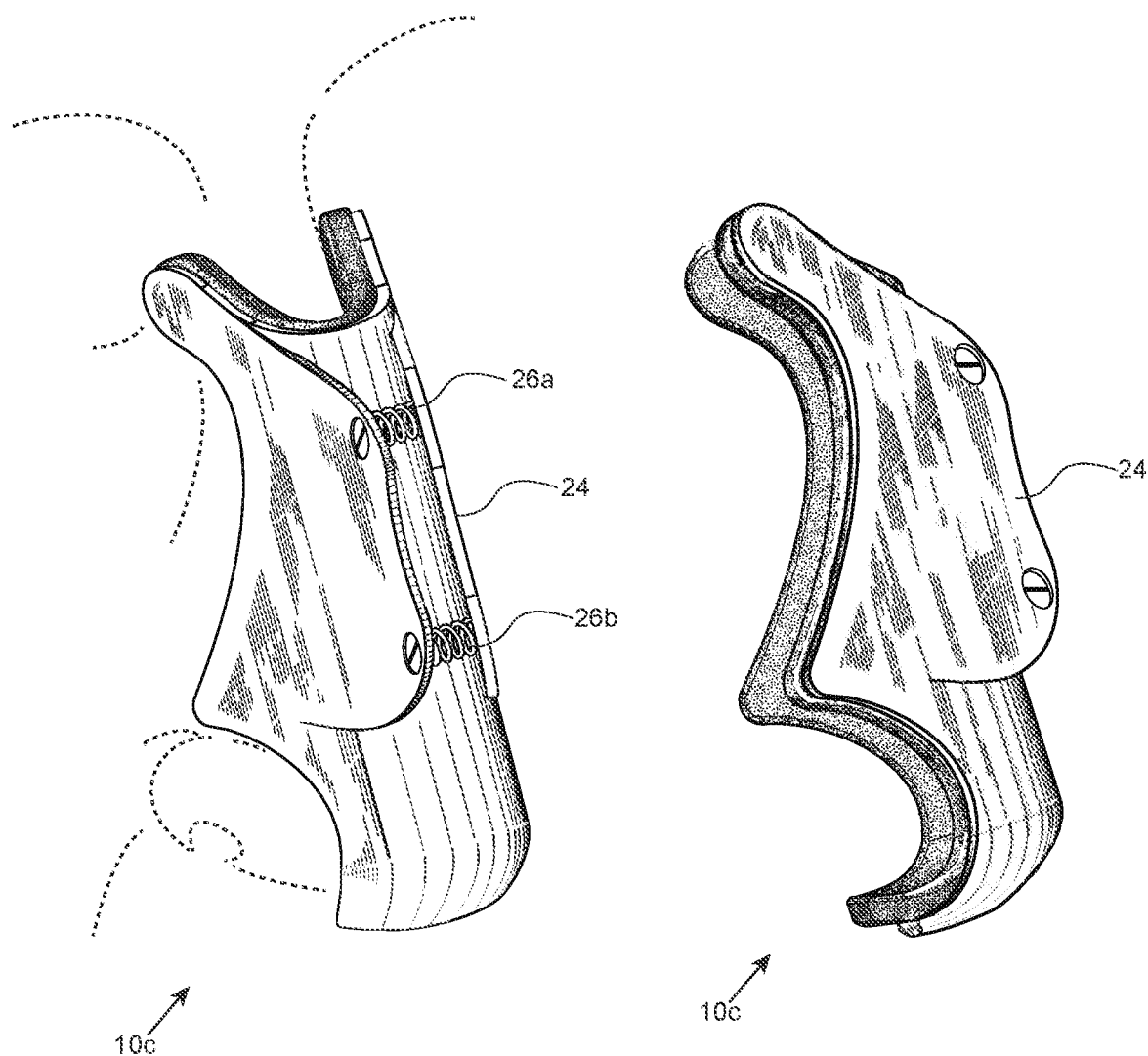
FIG. 5 is a front, top, and side perspective view of a third embodiment of the nasal splint device, illustrated positioned over a person's nose (shown by broken lines), with the nasal splint device comprising an outer layer serving as a semi-rigid frame over an inner layer that is flexible, soft, and/or malleable and configured to sit against or contour along the person's nose, the outer layer compressible by two identical compression springs, positioned between two opposing flanges of the outer layer and configured to vary the pressure applied on the nose.
FIG. 6 is a side perspective view of the third embodiment of the nasal splint device.
Figure 9:
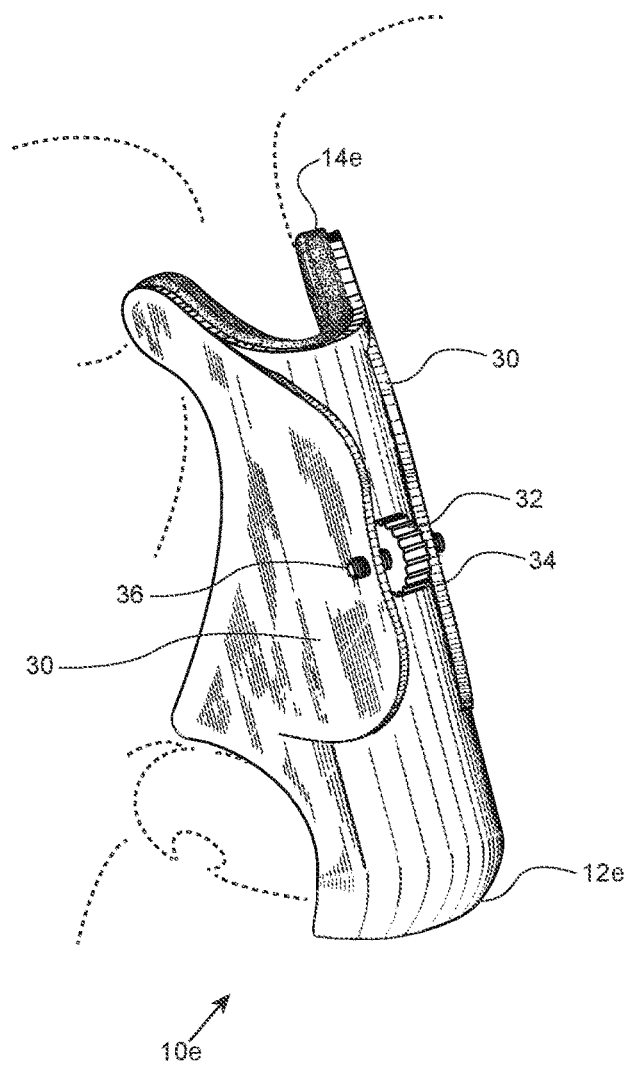
FIG. 9 is a front, top, and side perspective view of a fifth embodiment of the nasal splint device illustrated positioned over a person's nose (shown by broken lines), with the nasal splint device comprising an outer layer serving as a semi-rigid frame over an inner layer that is flexible, soft, and/or malleable and configured to sit against or contour the exterior of the patient's nose, the outer layer with two projecting flanges held by a knurled-nut mechanism between them, configured to move the projecting flanges to vary the pressure applied on the nose.
Figure 10:
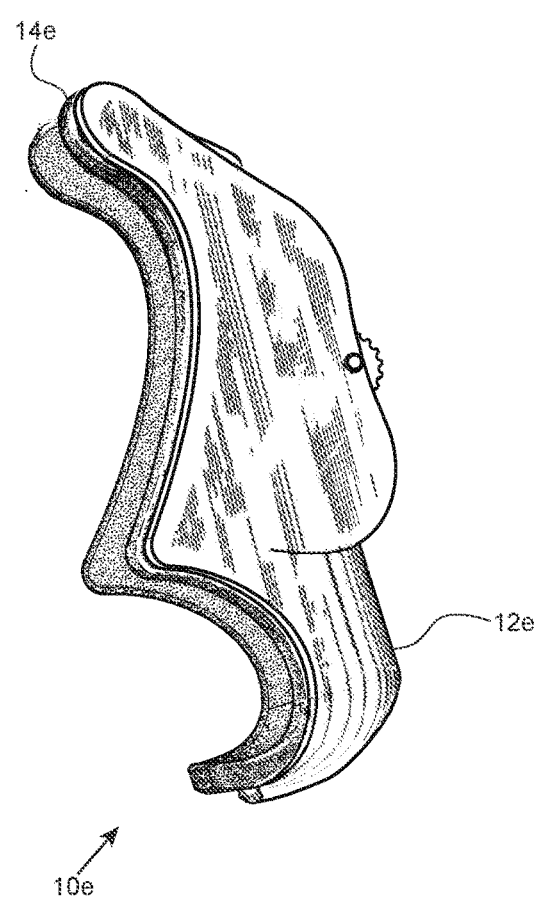
FIG. 10 is a side perspective view of the fifth embodiment of the nasal splint device.

In accordance with a third embodiment illustrated in FIGS. 5 and 6, the nasal splint 10c is adapted to be positioned over a person's nose such that it's outer layer 12c serves as a semi-rigid frame over an inner layer 14c that is flexible, soft, and/or malleable and configured to sit against or contour along the patient's nose, the outer layer 12c with two projecting flanges 24 (on either side) held by two springs 26a and 26b between them, configured to move the projecting flanges 24 to vary the pressure applied on the nose. The two springs 26a and 26b are coiled springs held substantially in place by an eye at either end with a nut. Applying a slight force on the protecting flanges 24 to compress the distance between the projecting flanges 24 can help position the nasal splint 10c over a patient's nose. The third embodiment may be constructed from similar materials as those described for embodiments one and two.

In accordance with a fourth embodiment, the nasal splint 10d is positioned over a patient's nose such that an outer layer 12d serves as a semi-rigid frame over an inner layer 14d that is flexible, soft, and/or malleable and configured to sit against or contour along the patient's nose, the outer layer 12d having a crimped surface and assembly 26 28 (at either end) configured to vary the pressure applied on a patient's nose. The crimped surface and assembly 28 create the biased forces to vary the pressure by the nasal splint 10 on the nose 15. The fourth embodiment may be constructed from similar materials as those described for embodiments one, two, and three.

In accordance with a fifth embodiment, the nasal splint device 10e is adapted to be positioned over a person's nose such that it's outer layer 12e serves as a semi-rigid frame over an inner layer 14e that is flexible, soft, and/or malleable and configured to sit against or contour along a patient's nose, the outer layer 12e with two projecting flanges 30 (on either side) held by a knurled-nut mechanism 32 between them, configured to move the projecting flanges 30 to vary the pressure applied on the nose. The knurled-nut mechanism 32 comprises a nut 34 and a grooved pin 36 over which the nut 34 rolls. Moving the nut 34 tightens or releases the pressure on the projecting flanges 30 by compressing or widening the distance between the projecting flanges 30. The fourth embodiment may be constructed from similar materials as those described for embodiments one, two, three, and four.

The width, length and peripheral outline or edges of the various embodiments of the nasal splint 10 may be defined by the base or inner layer (e.g., 14a), cover or outer layer (e.g., 12a), or a combination of any two or more layers or portions thereof. The base or inner layer 14a and cover or outer layer 12a of nasal splint 10 may have like or dissimilar dimensions or peripheral edges, in whole or in part, compared to each other. Their respective peripheral shapes may be uniform or non-uniform, and may also be of like or dissimilar size or scale. Portions of any layer may define a horizontal region of the nasal splint 10 or a portion thereof. Furthermore, the base or inner layer (e.g., 14a) and cover or outer layer 12a of nasal splint 10 may be interchanged in portions. The base or inner layer (e.g., 14a) and cover or resilient layer (e.g., 12a) may have identical peripheral edges, and thus may be formed as a single unit. Portions of one or both flat surfaces of any layer, member or component thereof, may overlap portions of any flat surface of another layer. Preferably, however, the base or inner layer (e.g., 14a) layer acts as a buffer in engaging the user's skin, as described here, and portions of one or more nasal splint layers may engage nasal outer wall tissues simultaneously. When engaged on the nose 15 of a wearer, preferably no portion of a layer extends substantially over a skin surface area beyond those surface areas associated with the nasal passages as described here.

Nasal splints 10 may be typically die cut from a continuous laminate of material layers. However, nasal splint layers, members or components thereof, material separations or horizontal regions may be formed or die cut, in whole or part, from one or more of continuous materials before, or during, assembly of the material laminate from which finished nasal splint 10 are die cut. In fabricating nasal splints 10, end regions and projections are preferably formed as mirror images of each other. However, asymmetric or non-identical end region configurations have the advantage of providing disparate forces if required.

The nasal splint 10 is configured with the outer and resilient layer (e.g., 12a), which has resilient properties provided through its resilient layer and is configured to provide suitable spring return biasing force as described here. Overall spring biasing force is generally determined by the width, length, and thickness of at least one resilient member or the resilient layer as a whole from its constituent member(s) and/or components. Resilient member preferably has an adhesive substance disposed on at least a portion of at least one of two opposite flat surface sides for engaging or laminating it to other layers, members or components of the nasal splint 10 or for engaging the skin surface of the nose 15. Resilient member has opposite terminal ends that may conform to at least portions of the lateral end edges of the outer layer of the nasal splint 10. The nasal splint 10 includes means to direct its resilient properties. The means may comprise configuration of, or modification to, the resilient layer or the material from which the resilient layer is formed. The configuration or modification may be made either in the course of forming the inner or resilient layer, or may be made to the outer or resilient layer material separately, or at the time the material is assembled into the continuous material laminate from which nasal splint 10 is die cut (i.e., at the time the vertical laminate of nasal splint 10 is formed). The configuration or modification may include cuts, notches, openings, or the like formed in the outer resilient layer material as required; or by varying the finished dimensions of the resilient member or a component thereof, such as by forming a gradiently-tapered width; or by peripheral shape of the resilient member, such as by extensions or divergent spring finger components extending outward from its longitudinal extent; or by more than one resilient member, each member contributing a portion of the total spring biasing force. Having divergent spring fingers or multiple resilient members may increase the effective surface area subject to resilient layer spring biasing forces by spreading those forces to a greater, primarily lateral, surface area of nasal splint 10.

The disclosed embodiments of the nasal splint 10 may be constructed by a 3D printing process or additive manufacturing, which is the process for building a three-dimensional object from a computer-aided design (CAD) model, by successively adding material layer by layer, unlike conventional machining, casting and forging processes, where material is removed from a stock item (subtractive manufacturing) or poured into a mold and shaped by means of dies, presses and harmers. 3D printing processes cover a variety of processes by which material is joined or solidified under computer control to create the various embodiments of the nasal splint 10, with material being added together (such as liquid molecules or powder grains being fused together, typically layer by layer. The precision accomplished by these processes have made them viable as industrial-production technology for products. One of the key advantages of using these processes is the ability to produce the shapes and geometries of the various embodiments.

The illustrations depicted here may be used to create a 3D model or CAD file to initiate the process of manufacture. The digital 3D-model is saved in STL (stereolithography file) format and is then sent to a 3D printer. The 3D printer prints the design layer by layer to form a real object. There are several 3D printing technologies. The main differences are how layers are built to create parts. 3D printing technologies include SLS (selective laser sintering), FDM (fusion deposition modeling) and SLA (stereolithography). Selective laser sintering (SLS) and fused deposition modeling (FDM) use melted or softened materials to produce layers. The selective laser sintering (SLS) process melts fine powders, bit by bit, into 3D shapes. Fused deposition modeling printers use a thermoplastic filament, which is heated to its melting point and then extruded, layer by layer, to create the nasal splint 10. The materials that may be used in this process to create the nasal splint 10 include basic material ABS, such as Acrylonitrile Butadiene Styrene, polyamide, polycarbonate, polyethylene, polypropylene. Many different materials may be used for 3D printing, such as ABS plastic, PLA, polyamide (nylon), glass filled polyamide, stereolithography materials (epoxy resins), silver, titanium, steel, wax, photopolymers and polycarbonate.

Models may be created by using software such as Google SketchUp, to draw edges and faces and using the push/pull tool to extrude any flat surface into a 3D form. Alternatively, the software 3Dtin may be used to draw directly from a browser. OpenSCAD is another software that may be used, which focuses on the CAD aspects. Tinkercad is another quick way to create designs, with only three basic tools that may be used to create the various embodiments. Once the model is created, the STL file may be downloaded and the 3D print process started. Alternatively, commercial software such as CAD software AutoCAD and Pro Engineer and software packages Rhino, Maya, and SolidWorks may be used to design 3D models.

The foregoing descriptions and illustrations are intended to reveal the scope and spirit of the present invention and should not be interpreted as limiting, but rather as illustrative of the inventive concepts and techniques thereof. One of ordinary skill in the art to which the present invention is directed will appreciate that insubstantial changes, modifications and alterations of the present disclosure may be made and each such insubstantial change, modification and alteration are intended to be fully covered hereby.

What is claimed is:

1. A plurality of different types of nasal splints, comprising:
    an outer layer providing a single semi-rigid frame over a flexible inner layer, said outer layer configured for covering and contouring a surface area of a human nose, said single semi-rigid frame of said outer layer comprising:
        two opposing flanges, each configured for contouring outer-wall-nasal tissue of the human nose to vary an inward pressure applied on the human nose; said single semi-rigid frame interconnecting said two opposing flanges, said single semi-rigid frame including a mechanism positioned within said two opposing flanges, said mechanism configured to apply a force to vary inward pressure on said two opposing flanges, said mechanism configured in a first constructed form in a first type of nasal splint to include a spring assembly with coiled springs configured to apply a selectable spring-biased force to vary the inward pressure on the human nose, the coiled springs held substantially in place by an eye with a nut at either end, to maintain force between two opposing sides and said mechanism configured in a second constructed form in a second type of nasal splint to include a crimped surface and assembly within said single semi-rigid frame of said outer layer, said crimped surface and assembly configured to vary the inward pressure applied on the human nose, said single semi-rigid frame configured to include said first constructed form in an application requiring said selectable spring-biased force and wherein said mechanism is constructed in a third form in a third type of nasal splint by compressing an upper end of said two opposing flanges by two springs extending parallel to each other and configured for applying the selectable spring-biased force to vary the inward pressure on the human nose and wherein said mechanism is constructed in a fourth form in a fourth type of nasal splint including a knurled device placed between the two opposing flanges, said knurled device configured for applying the selectable spring-biased force to vary the inward pressure on the human nose;

said flexible inner layer sized to cover an inner periphery of said single semi-rigid frame; and said outer layer being of similar size as said flexible inner layer, said outer layer positioned directly over said flexible inner layer.

2. The plurality of different types of nasal splints of claim 1, wherein the flexible inner layer is malleable and configured from a nonwoven synthetic fabric.

3. The plurality of different types of nasal splints of claim 1 wherein said mechanism includes the crimped surface and assembly within said single semi-rigid frame of said outer layer configured to vary the inward pressure applied on the human nose, wherein the crimped surface and assembly are constructed from at least one from a group of: acrylonitrile butadiene styrene, polyamide, polycarbonate, polyethylene, polypropylene, ABS plastic, PLA, polyamide, glass filled polyamide, stereolithography materials, silver, titanium, steel, wax, photopolymers and polycarbonate.

4. The plurality of different types of nasal splints of claim 1, wherein said coiled springs apply varying pressure responsive to pressure applied on the opposing flanges and wherein the selectable spring-biased force is based on a width, length, and thickness of the outer layer.

5. The plurality of different types of nasal splints of claim 1, wherein said flexible inner layer is made of a soft material.

6. The plurality of different types of nasal splints of claim 1, wherein said outer layer is made of a resilient material.

7. The plurality of different types of nasal splints of claim 1, wherein each type of nasal splint is die cut from a continuous laminate of material layers.

8. A plurality of different types of nasal splints, comprising:

a single outer layer providing a semi-rigid frame extending over a flexible inner layer, said single outer layer configured for covering and contouring a surface area of a human nose, said semi-rigid frame of said single outer layer comprising:

two opposing flanges, each configured for contouring outer-wall-nasal tissue of the human nose to vary an inward pressure applied on the human nose;

said semi-rigid frame interconnecting said two opposing flanges, said semi-rigid frame including a mechanism constructed in different forms and positioned within said two opposing flanges, said mechanism configured to apply a force to vary the inward pressure on said two opposing flanges, said mechanism configured in a first constructed form to apply a selectable spring-biased force, wherein said mechanism configured in the first constructed form includes two tubular springs positioned in parallel and extending along a length of the semi-rigid frame of said single outer layer to apply the selectable spring-biased force, wherein the two tubular springs are identical compression springs configured to flank either side of a top of the human nose and run a length of the human nose and wherein said mechanism constructed in an alternative second constructed form includes a flat spring positioned over said single outer layer, said flat spring configured for compressing said single outer layer to apply a selectable spring-biased force to vary the inward pressure applied on the human nose and said mechanism configured in an alternative third constructed form includes a crimped surface and assembly within said semi-rigid frame of said single outer layer configured to vary the inward pressure applied on the human nose, and wherein said mechanism is constructed in a fourth constructed form including a knurled device placed between the two opposing flanges, said knurled device configured for applying the selectable spring-biased force to vary the inward pressure on the human nose, wherein said mechanism is usable in the first constructed form, the alternative second constructed form, the alternative third constructed form, and the fourth constructed form, in particular instances of use; said flexible inner layer sized to cover an inner periphery of said semi-rigid frame; and said single outer layer being of similar size as said flexible inner layer, said single outer layer positioned directly over said flexible inner layer.

9. The plurality of different types of nasal splints of claim 8, wherein the single outer layer is made of a biaxially oriented polyester resin.

10. The plurality of different types of nasal splints of claim 9, wherein the single outer layer has a thickness that is at least one from 0.005", 0.007", and 0.010".

11. The plurality of different types of nasal splints of claim 8, wherein the inner layer is malleable and configured from a nonwoven synthetic fabric.

12. The plurality of different types of nasal splints of claim 8, wherein each type of nasal splint is die cut from a continuous laminate of material layers.

13. The plurality of different types of nasal splints of claim 8, wherein the single outer layer is made of a resilient material.

14. The plurality of different types of nasal splints of claim 8, wherein the flexible inner layer is made of a soft material.

15. A method for making multiple different types of nasal splints, comprising:

configuring a nasal splint with a single outer layer that forms a semi-rigid frame over a flexible inner layer for covering and contouring a surface area of a human nose, wherein the semi-rigid frame is configured with two opposing flanges, each configured for contouring outer-wall-nasal tissue of the human nose to vary pressure applied on the human nose;

interconnecting the two opposing flanges;

positioning a mechanism within the two opposing flanges to apply a force to vary pressure on the two opposing flanges, wherein the mechanism is configured in a plurality of different forms including one constructed form to form a first type of nasal splint to include a spring assembly configured to apply a selectable spring-biased force to vary an inward pressure on the human nose, the selectable spring-biased force applied by a coiled spring held substantially in place by an eye with a nut at either end, to maintain force between two opposing sides and wherein the mechanism is configured in alternative constructed forms to form a second type of nasal splint, a third type of nasal splint, and a fourth type of nasal splint, the second type of nasal splint including a crimped surface within the semi-rigid frame of the single outer layer, the crimped surface configured to vary inward pressure applied on the human nose, the third type of nasal splint including a flat spring positioned over said single outer layer, said flat spring configured for compressing said outer layer to apply a selectable spring-biased force to vary the inward pressure applied on the human nose and the fourth type of nasal splint including a knurled device placed between the two opposing flanges, said knurled device configured for applying the selectable spring-biased force to vary the inward pressure on the human nose, the mechanism configured to include the one constructed form for use in a first particular instance requiring the selectable spring-biased force and the mechanism configured to include the alternative constructed forms for use in a second and other particular instances;

configuring the flexible inner layer in size to cover an inner periphery of the semi-rigid frame, the single outer layer being of similar size as the flexible inner layer, the single outer layer positioned directly over the flexible inner layer.

16. The method of claim 15, wherein the flexible inner layer is made of a soft material.

17. The method of claim 15, wherein the single outer layer is made of a resilient material.

18. The method of claim 15, wherein the crimped surface is constructed from at least one from a group of: acrylonitrile butadiene styrene, polyamide, polycarbonate, polyethylene, polypropylene, ABS plastic, PLA, polyamide, glass filled polyamide, stereolithography materials, silver, titanium, steel, wax, photopolymers and polycarbonate.

19. The method of claim 15, wherein each type of nasal splint is die cut from a continuous laminate of material layers.

20. The method of claim 15, further comprising:
determining the selectable spring-biased force by a width, length, and thickness of the single outer layer.

* * * * *